United States Patent [19]

Robbins et al.

[11] 4,082,612

[45] Apr. 4, 1978

[54] PLASMINOGEN ACTIVATOR COMPLEX

[75] Inventors: Kenneth C. Robbins, Chicago; Louis Summaria, Villa Park, both of Ill.

[73] Assignee: Michael Reese Research Foundation, Chicago, Ill.

[21] Appl. No.: 726,142

[22] Filed: Sep. 24, 1976

[51] Int. Cl.$^2$ .................... C07G 7/026; A61K 37/48
[52] U.S. Cl. .................................. 195/62; 195/66 B; 424/94
[58] Field of Search ................... 195/66 B, 62; 424/94

[56] References Cited

U.S. PATENT DOCUMENTS 3,865,692  2/1975  Holleman et al. ................. 195/66 B

OTHER PUBLICATIONS

Robbins et al., Journal of Biological Chemistry, vol. 248, No. 5, pp. 1631–1633 (1973).

*Primary Examiner*—Lionel M. Shapiro
*Attorney, Agent, or Firm*—Dressler, Goldsmith, Clement, Gordon & Shore, Ltd.

[57] ABSTRACT

A functionally active fraction of plasmin is provided which is capable of forming with streptokinase a complex with plasminogen activator activity.

The fraction is made by reducing the disulfide bonds of plasmin molecules while inhibiting the serine protease activity of the plasmin and separating the light (B) chain fraction from the reaction product.

32 Claims, No Drawings

PLASMINOGEN ACTIVATOR COMPLEX

The invention described herein was made in the course of work under a grant or award from the Department of Health, Education, and Welfare.

This invention relates to a functionally active fraction of plasmin and to complexes of this functionally active fraction with materials, such as streptokinase, which activate the plasmin fraction to form a substance which dissolves fibrin-containing blood clots. In particular, it relates to a plasmin fraction complex which has useful fibrinolytic activity even after its blood-derived components have been subjected to heat treatment for inactivation of viral contaminants.

BACKGROUND OF THE INVENTION

It is known that blood clots are formed through the action of a plasma component known as fibrin.

It is also known that materials which tend to dissolve fibrin (fibrinolytic materials) are effective in reducing, or eliminating, blood clots in the circulatory system where great harm can result from circulatory blockages which may be produced by undissolved blood clots.

Human blood contains plasminogen which is not an enzyme but an enzyme precursor. Certain activators convert plasminogen to plasmin which is capable of dissolving fibrin and breaking up clots. Plasmin is a proteolytic enzyme having a serine protease active site and having the capability of dissolving protein, including itself. Plasmin and many of its complexes are therefore unstable in storage in solution form without the addition of stabilizing materials, such as leupeptin. The proteolytic activity of plasmin and its complexes can produce adverse secondary effects when such materials are introduced into the bloodstream since proteolytic activity can destroy serum proteins, such as clotting and complement components.

Streptokinase, derived from streptococcus cultures, is an activator capable of converting human plasminogen to human plasmin. It is also capable of converting cat plasminogen to cat plasmin, but is relatively inactive for the conversion of other mammalian plasminogens.

When streptokinase is added to human plasminogen, its first action is to combine with some of the plasminogen in stoichiometric proportions to form a complex. The streptokinase-plasminogen complex then serves as a catalyst for conversion of the remaining plasminogen to plasmin. Streptokinase also combines stoichiometrically with plasmin to form a complex which is a catalyst for the conversion of plasminogen.

Streptokinase, as indicated above, is relatively inactive for the conversion of mammalian plasminogens other than human and cat plasminogens, and thus does not convert bovine plasminogen to bovine plasmin. On the other hand, the streptokinase-human plasminogen complex and the streptokinase-human plasmin complex are active in the conversion of bovine plasminogen to bovine plasmin.

It is known that plasmin may be split into a heavy (A) chain a light (B) chain by cleavage of the plasmin molecules at their interchain disulfide bonds (one or two disulfide bonds per molecule) and it is known that the heavy (A) chain and light (B) chain may be separated from each other. Rickli and Otavasky reported in *Eur. J. Biochem.* 59, 441–447 (1975) that the fractions may be separated by adsorption of the heavy (A) chain on a L-lysine-substituted polyacrylamide adsorbent with elution of the light (B) chain fraction. The authors do not report any properties of the eluted light (B) chain fraction, but our tests have shown that the light (B) chain fraction produced by their method, when complexed with streptokinase, produces a complex which is substantially inactive for the conversion of plasminogen to plasmin.

The heavy (A) fraction cannot produce streptokinase complex.

For safety reasons, therapeutic materials derived from human blood, including plasminogen and plasmin, cannot be injected into the bloodstream of a patient because such injection can transmit viral contaminants, such as the virus of hepatitis, to the bloodstream of the patient. The Food and Drug Administration of the United States requires that any material derived from human blood be heated at 60° C for ten hours to inactivate any hepatitis virus before it will approve the material, or any derivative thereof, for sale as a therapeutic material to be injected into the bloodstream.

Subjection of a streptokinase-plasmin complex to the above-described heat treatment alters its character and renders it inactive for conversion of plasminogen to plasmin. Subjection of plasminogen to the above-described heat treatment before converting it to plasmin and before complexing with streptokinase also alters the character of the resulting complex. Although its streptokinase complex still retains activity for the conversion of plasminogen to plasmin, its protein component is so denatured by the heat treatment that antigenic and pyrogenic reactions may be produced when the complex is injected into the bloodstream of a patient.

For these reasons, streptokinase-plasmin complexes have not been utilized as a standard therapeutic treatment for dissolving blood clots in human patients.

SUMMARY OF THE INVENTION

In accordance with the instant invention, a plasmin light (B) chain having a serine protease active site is produced. It has been found that the serine protease catalytic site on the plasmin molecule is on the light (B) side thereof but that the methods heretofore used to cleave the plasmin molecule and to thereafter separate the light (B) and heavy (A) chains inactivate the serine protease catalytic site on the light (B) chain so that the light (B) chain becomes as inactive as the heavy (A) chain (which has no such catalytic site).

It has further been found that known reversible serine protease active site inhibitors, such as leupeptin, inhibit the deactivation, or poisoning, of the serine protease catalytic site in the light (B) chain fraction and thereby protect its activity during the reduction and separation steps.

It has also been found that streptokinase protects the serine protease active site and that a streptokinase-plasminogen complex, or a streptokinase-plasmin complex, may be subjected to the reduction and separation steps without a reversible serine protease active site inhibitor being present to produce a streptokinase-light (B) chain fraction complex which has fibrinolytic activity.

Still further, it has been found that an active light (B) chain fraction may be prepared from a plasminogen starting material which has been heat treated at 60° C for ten hours and that the fraction thus prepared may be combined with streptokinase to produce a fibrinolytically active complex which may produce substantially less antigenic or pyrogenic reaction when injected into the blood stream of a patient than the complex of streptokinase with a heat treated plasminogen which has not been fractionated.

The method of the invention in its preferred aspect involves subjecting human plasminogen to an initial heat treatment at 60° C for ten hours to inactivate any viral contaminants therein. The heat treated plasminogen is then activated to plasmin and mixed with a serine protease active site inhibitor, such as leupeptin (acetyl-L-leucine-L-leucine-L-argininal) at a level to inhibit most or all of the plasmin activity. The plasminleupeptin mixture is then reduced with a reducing agent, such as 2-mercaptoethanol or dithioerythritol to cleave the disulfide bonds in the plasmin molecules resulting in the plasmin heavy (A) chains and the plasmin light (B) chains. The product is then alkylated with an alkylating agent, such as sodium iodoacetate to prevent the cleaved ends of the disulfide bonds (sulfhydryl groups) from recombining; and the alkylated product is passed through an affinity chromatography column in which the heavy (A) chain fraction is adsorbed and the light (B) chain fraction is eluted, passing through the column unadsorbed. The light (B) chain is precipitated with ammonium sulfate, centrifuged and then redissolved in a buffer medium. When the chain is precipitated, most of the leupeptin remains behind in the liquid phase. The small amount of leupeptin which stays with the precipitated and redissolved light (B) chain helps to preserve it when it is stored in liquid phase but does not impair its activity since it is diluted away to a negligible concentration when the plasmin light (B) chain complex with streptokinase (described below) is introduced into the bloodstream of a patient.

The light (B) chain is complexed with streptokinase, crude or purified, by mixing the materials together in equimolar proportions and then incubating the blend for a short period.

An equimolar light (B) chain-streptokinase complex can also be prepared from a plasmin-streptokinase complex by reducing the complex to cleave the disulfide bonds in the plasmin molecules of the complex, producing plasmin heavy (A) chains and plasmin light (B) chains bonded to the streptokinase, followed by alkylation and passage of the product through a chromatography column in which the plasmin heavy (A) fraction is adsorbed and the plasmin light (B) chain-streptokinase complex fraction is eluted, passing through the column unadsorbed.

In the latter case, the use of leupeptin, or other reversible serine protease active site inhibitors, is unnecessary since the streptokinase serves the same function and prevents the loss of activity in the light (B) chain during the reduction of the plasmin structure and during the separation steps.

The plasmin light (B) chain, prepared as described above, has much less proteolytic activity than the plasmin from which it is derived, generally less than about 5% on a molar basis and less than about 15% on a weight basis. Typically, the plasmin light (B) chain fraction has a proteolytic activity, measured on a casein substrate, from about 2 to 3 CTA units/mg protein, or from about 0.05 to 0.08 CTA units/nmol protein. CTA units are standard activity units adopted by the Committee on Thrombolyic Agents (National Heart and Lung Institute) and by the World Health Organization and are described in Johnson et al. Thrombosis et Diathesis Haemorrhagica, vol. 21, pp. 259–272 (1969).

The plasmin light (B) chain-streptokinase complex, prepared from a plasmin-streptokinase complex as described above, has much less proteolytic activity than the plasmin-streptokinase from which it is derived, generally less than about 20% on a molar basis and less than about 35% on a weight basis. Typically, the plasmin light (B) chain-streptokinase complex prepared from a plasmin-streptokinase complex has a proteolytic activity, measured on a casein substrate, from about 2 to about 3.5 CTA units/mg protein or from about 0.14 to about 0.25 CTA units/nmol protein.

The plasmin light (B) chain-streptokinase complex made from streptokinase and a light (B) chain, as described above, has a proteolytic activity or about the same magnitude as that of the plasmin light (B) chain-streptokinase complex made from a plasmin-streptokinase complex.

The plasmin light (B) chain-streptokinase complex, made from the plasmin-streptokinase complex as described above, typically has a bovine plasminogen activator activity from about 1.6 to about 1.8 times as great, on a weight basis, as that of the plasmin-streptokinase complex from which it is made. On a molar basis the bovine plasminogen activity of the light (B) chain-streptokinase complex is about 0.8 to 1.0 times as great as that of the plasmin-streptokinase complex from which it is made. Typical values for the bovine plasminogen activator activity of the plasmin light (B) chain-streptokinase complexes made from a plasmin-streptokinase complex, measured on a casein substrate, are from about 3 to about 4 CTA units/mcg protein, or from about 200 to about 260 CTA units/nmol protein.

The bovine plasminogen activator activity of the plasmin light (B) chain-streptokinase complex made from streptokinase and a plasmin light (B) chain, as described above, is from about 0.70 to about 0.75 of the activity of the plasmin light (B) chain-streptokinase complex made from a plasmin-streptokinase complex.

The human plasminogen activator activity of the plasmin light (B) chain-streptokinase complex made from the plasmin-streptokinase complex, as described above, has generally from about 1.8 to about 2.2 times the activity, on a weight basis, of the plasmin-streptokinase complex from which it is made. On a molar basis, the human plasminogen activator activity of the plasmin light (B) chain-streptokinase complex is from about 1.0 to about 1.2 times the activity of the plasmin-streptokinase complex from which it is made.

Typical values for the human plasminogen activator activity of the plasmin light (B) chain-streptokinase complex measured on a casein substrate, are from about 8 to about 12 CTA units/mcg protein, or from about 550 to about 800 CTA units/nmol protein.

The human plasminogen activator activity values for the plasmin light (B) chain-streptokinase complexes made from a plasmin light (B) chain and streptokinase are from about 0.9 to about 1.0 times the values of the plasmin light (B) chain-streptokinase complex made from a plasmin-streptokinase complex.

The substantially higher human plasminogen activator activity of the plasmin light (B) chain-streptokinase complex, on a weight basis, as compared to the activity of the plasmin-streptokinase complex makes it possible to utilize lower intravenous dosages of the plasmin light (B) chain-streptokinase complex to achieve a desired fibrinolytic effect, as compared to the plasmin-streptokinase complex.

In addition, in vitro tests have shown the plasmin light (B) chain-streptokinase is substantially more effective than the plasmin-streptokinase complex in reducing, or dissolving blood clots even at dosages which are comparable with respect to human plasminogen activator activity. While it is not desired to be bound by any particular theory, it is believed that this enhanced effectiveness is due to the smaller molecular size of the plasmin light (B) chain-streptokinase complex as compared to the plasmin-streptokinase complex and to the consequent superior ability of the smaller molecules to penetrate into and act upon the interior of a blood clot structure.

When it is desired to assure the absence of viral contaminants in the plasmin light (B) chain of one aspect of this invention or in the plasmin light (B) chain-streptokinase complex of another aspect of this invention, the plasminogen starting material is heat treated to inactivate any viral contaminants prior to being converted to plasmin or complexed with streptokinase. A standard heat treatment, required by the United States Food and Drug Administration as explained above, is one in which the plasminogen is maintained at a temperature of at least 60° C for at least ten hours. It has been found that the plasmin light (B) chain of one aspect of this invention and the plasmin light (B) chain-streptokinase complex of another aspect of this invention retain substantially all of their respective activities even when the respective products are prepared from heat treated plasminogen as a starting material.

When a plasmin-streptokinase complex is made from a heat treated plasminogen starting material, it, too, retains substantially all of its activity. However, the action of the heat on the plasminogen molecule alters, or denatures, its structure at a number of sites and the relatively large plasmin molecule derived therefrom is also substantially denatured, tending to make it and its complexes antigenic and pyrogenic when introduced into the bloodstream of a patient.

When plasmin prepared from heat treated plasminogen is reduced and split into a heavy (A) chain fraction and a light (B) chain fraction, and the heavy (A) chain fraction is discarded, many of the denatured sites, which are on the heavy (A) chain fraction, are also discarded, leaving a native light (B) chain fraction which could be substantially less antigenic and less pyrogenic than the total denatured plasmin. Similarly, complexes with such a plasmin light (B) chain fraction, such as streptokinase complexes, could be substantially less antigenic and less pyrogenic than similar complexes from the total denatured plasmin.

It has been found that it is not necessary to use highly purified streptokinase since crude streptokinase fractions can also be used in preparing the complexes. In effect, the coupling reaction of the streptokinase with the plasmin light (B) chain fraction, or with the total plasmin, serves to separate the streptokinase from the impurities associated with it in its crude form.

EXAMPLE 1

Preparation of Light (B) Chain 150 mg of leupeptin is added to 10 ml of human plasmin (25–30 CTA units/mg protein), in solution in an aqueous buffer medium comprising 25% of glycerol, 0.04 mols/liter of Tris (hydroxymethyl)aminomethane (hereinafter called "Tris"), 0.02 mols/liter of lysine and 0.08 mols/liter of sodium chloride at pH 9 and at a concentration of 5 mg/ml of protein. The plasmin was prepared from heat treated human plasminogen, as described below. During the addition of the leupeptin, the plasmin solution was maintained in a 0° C ice bath; and the final concentration of the leupeptin in the solution is 0.04 mols/liter.

To this plasmin-leupeptin mixture, 0.072 ml of concentrated 2-mercaptoethanol is added (final concentration of 0.1 M) and the plasmin-leupeptin mixture is reduced for 20 minutes while maintained in a 20° C water bath.

The reduced plasmin is then placed in 0° C ice bath, and 0.29 ml of 4 M sodium iodoacetate is added to alkylate the sulfhydryl groups produced by rupture of the disulfide bonds in the plasmin molecules during the reduction reaction. The alkylation reaction is permitted to proceed for 30 minutes at 0° C.

The reduced and alkylated plasmin is then passed through an L-lysine-substituted Sepharose column (1 × 20 cm), equilibrated and eluted with a 0.1 M sodium phosphate buffer at a pH of 7.4 and at 2° C. The elution proceeds at a flow rate of 60 ml/hr and fractions of 3 ml/volume are separately collected. The light (B) chain passes through the column unadsorbed and is monitored by absorbance measurements at 280 nm. When the absorbance reading returns to 0, the fractions containing the light (B) chain are pooled and ammonium sulfate, 3.1 g/10 ml, is added at 0° C to precipitate the light (B) chain and leave the unprecipitated leupeptin in the liquid phase. The pooled fractions containing ammonium sulfate are permitted to stand overnight at 4° C to assure complete precipitation of the light (B) chain and the precipitate is thereafter removed by centrifugation at 6000 RPM for one hour at 2° C.

The light (B) chain precipitate is dissolved to a concentration of 10 mg/ml ($E_{1cm}^{1\%} = 16$) in an aqueous buffer medium similar to that used initially to dissolved plasmin. The light (B) chain is clarified at 3000 RPM for 1 hour at 2° C and is stored at −20° C.

Typically, the plasmin light (B) chain thus obtained has a proteolytic activity on a casein substrate of 0.07 CTA units/nmol protein or 2.6 CTA units/mg protein, as compared to a proteolytic activity of 2.03 CTA units/nmol protein or 27.2 CTA units/mg protein for the plasmin from which the light (B) chain is derived.

Typically, the plasmin light (B) chain thus obtained can incorporate 0.09 mols of tritiated diisopropylphosphorofluoridate per mol of protein as compared to the starting plasmin which can incorporate 0.95 mols per mol of protein.

EXAMPLE 2

Preparation of Plasmin Light (B) Chain-Streptokinase Complex from Light (B) Chain An equimolar plasmin light (B) chain-streptokinase complex is prepared by adding 0.5 ml of streptokinase (32 mg/ml) to 0.9 ml of the light (B) chain preparation of Example 1. The equimolar complex is incubated at 25° C for 10 minutes and then stored at −20° C.

Typically, the equimolar complex thus prepared has a proteolytic activity on a casein substrate of 0.16 CTA units/nmol protein or 2.3 CTA units/mg protein, as compared to a proteolytic activity of 1.52 CTA units/nmol protein or 11.6 CTA units/mg protein for the streptokinase equimolar complex prepared with the starting plasmin.

Typical bovine plasminogen activator activity levels for the equimolar complex of Example 2 on a casein substrate are 2.6 CTA units/mcg protein or 175 CTA units/nmol protein, as compared to 2.1 CTA units/mcg protein or 264 CTA units/nmol protein for the streptokinase equimolar complex with the starting plasmin.

For human plasminogen activator activity, typical levels for the equimolar complex of Example 2 on a casein substrate are 9.3 CTA units/mcg protein or 636 CTA units/nmol protein, as compared to 4.9 CTA units/mcg protein or 622 CTA units/nmol protein for the streptokinase equimolar complex with the starting plasmin.

Typically, the equimolar complex of Example 2 can incorporate 0.50 mols of tritiated diisopropylphosphorofluoridate per mol of protein as compared to a level of 0.90 mols per mol of protein for an equimolar complex of streptokinase with the starting plasmin.

EXAMPLE 3

Preparation of Plasmin Light (B) Chain-Streptokinase Complex from Plasmin-Streptokinase Complex Heat treated human plasminogen, (25-30 CTA units/mg protein) is dissolved in an aqueous buffer medium containing 0.05 mols per liter of Tris, 0.02 mols per liter of lysine and 0.1 mols per liter of sodium chloride having a pH of 9 to a concentration of 22 mg/ml of protein. To 3 ml of the aforementioned plasminogen solution in a 0° C water bath, there is added 1 ml of streptokinase (100,000 units/mg of protein) at a concentration of 32 mg/ml of protein in a 0.067 M sodium phosphate buffer at a pH of 7.4. The mixture is incubated in a 25° C water bath for 10 minutes to allow the complex to convert to a plasmin-streptokinase complex. The complex is then cooled in 0° C ice bath and diluted to 12 ml by adding 8 ml of the 25% glycerol buffer solution described in Example 1.

To 12 ml of the plasmin-streptokinase complex, prepared as described above, there is added 0.07 ml of concentrated 2-mercaptoethanol to a final concentration of 0.1 M. The complex is reduced for 20 minutes in a 20° C water bath, then cooled to 0° C, and alkylated by the addition of 0.35 ml. of 4 M sodium iodoacetate. After standing for 30 minutes at 0° C, the reduced and alkylated streptokinase complex is passed through an L-lysine substituted-Sepharose column (1 × 20 cm) in the same manner as is described in Example 1 for the reduced and alkylated plasmin. The light (B) chain-streptokinase complex passes unadsorbed through the column and is monitored, collected, precipitated, centrifuged, dissolved and clarified in the same manner as the light (B) chain in Example 1.

Typically, the plasmin light (B) chain-streptokinase complex of Example 3 has a proteolytic activity on a casein substrate of 0.21 casein units/nmol protein or 2.9 CTA units/mg protein, as compared to a proteolytic activity of 1.52 CTA units/nmol protein or 11.6 CTA units/mg protein for the streptokinase equimolar complex with the starting plasmin.

Typical bovine plasminogen activator activity levels for the complex of Example 3 on a casein substrate are 3.6 CTA units/mcg protein or 237 CTA units/nmol protein, as compared to 2.1 CTA units/mcg protein or 264 CTA units/nmol protein for the streptokinase equimolar complex with the starting plasmin.

For human plasminogen activator activity, typical levels for the complex of Example 3 on a casein substrate are 10.0 CTA units/mcg protein or 685 CTA units/nmol protein, as compared to 4.9 CTA units/mcg protein or 622 CTA units/nmol protein for the streptokinase equimolar complex with the starting plasmin.

Typically, the complex of Example 3 can incorporate 0.70 mols of tritiated diisopropylphosphorofluoridate per mol of protein as compared to a level of 0.90 mols per mol of protein for an equimolar complex of streptokinase with the starting plasmin.

EXAMPLE 4

Heat Treatment of Plasminogen

In Example 1, the starting plasmin is described as "prepared from heat treated human plasminogen" and in Example 3 the starting plasminogen is described as "heat treated."

In each case, human plasminogen, at a concentration of 20 mg/ml in a 0.05 M Tris-0.02 M lysine-0.1 M NaCl buffer at a pH of 9.0, is adjusted at 0° C to pH 3.0 with 1N HCl, then dialyzed extensively against a 0.15 M glycine-0.001 M HCl buffer at a pH of 3.0. After dialysis, the protein solution is diluted with the 0.15 M glycine-0.001 M HCl buffer to a final concentration of 1 mg protein per ml. and heated in a stoppered flask, in a water bath at 60° C for 10 hours. The plasminogen is then cooled in an ice bath and precipitated out by the addition of solid ammonium sulfate (3.1 g/10 ml solution). The heat treated plasminogen is recovered by centrifugation at 6000 RPM for 1 hour, and the precipitate is dissolved to a concentration of 10 mg/ml in the 0.05 M Tris-0.02 M lysine-0.10 M NaCl buffer at a pH of 9.0. The heat treated plasminogen concentrate is clarified at 3000 RPM for 1 hour and insoluble protein was removed, and discarded. The plasminogen is further purified with an L-lysine-substituted Sepharose affinity chromatography column, and after elution with ε-aminocaproic acid is recovered by the ammonium sulfate precipitation method. Approximately 74% of the initial protein and 73% of the initial proteolytic activity is recovered after the heat treatment, with almost no change in the specific activity of the plasminogen.

It is to be understood that the procedures of the foregoing examples may be modified without departing from the invention.

For example, other reversible serine protease active site inhibitors, such as benzamidine, and its derivatives may be used in place of leupeptin. The serine protease active site inhibitor is preferably used at a concentration sufficient to provide about 90% plasmin inhibition. With benzamidine as the serine protease active site inhibitor, the proteolytic activities of the light (B) chain and of its streptokinase complex are not as low as those of the products produced using a leupeptin inhibitor but are lower than those of the streptokinase complex with whole plasmin. Plasminogen activator activity is also higher for the products produced using benzamidine as the serine protease active site inhibitor up to about 8 CTA units/mcg of protein or 600 CTA units/nmols for bovine plasminogen activator activity, or up to about 25 CTA units/mcg of protein or 1500 CTA units/nmol for human plasminogen activator activity.

In place of 2-mercaptoethanol, other reducing agents, such as dithioerythritol or dithiothreitol, may be used to cleave the disulfide linkages in the plasmin molecules.

The alkylating agent may be sodium iodoacetate, as shown in Examples 1 and 3, but may also be iodoacetamide, or any other alkylating agent known to provide a protective group on a free sulfhydryl group.

The plasminogen starting material need not be pure. Crude preparations comprising plasma fractions or even total plasma, may be used since purification will take place during the further processing of the material.

In place of L-lysine-substituted Sepharose in the affinity chromatography column, other selective adsorbents, such as L-lysine-substituted polyacrylamide or L-lysine-substituted agarose may be used, as well as Sepharose, polyacrylamide or agarose, substituted by L-arginine or D-lysine. The chromatographic separation may be carried out by a batch technique rather than in a column, if desired.

While the invention has been described with respect to the equimolar complex of the plasmin light (B) chain with streptokinase, it is to be understood that the plasmin light (B) chain will also form useful complexes with all other substances which form equimolar complexes with human plasminogen to produce an activator, e.g. staphylokinase. Such complexes are made in the manner described above for the complexes with streptokinase and are similarly useful for their fibrinolytic activity.

The equimolar complexes of this invention, when administered to a patient for fibrinolytic action, are best administered intravenously. They may be administered gradually, over an extended period, in dilute form in a physiological glucose-saline solution or may be administered in a more concentrated form dissolved in physiological glucose-saline solution, alone or mixed with other materials such as human albumin. Dosages may vary, depending on the condition of the patient but would generally be in the range of 0.01–1.0 mg/kilo of body weight/day.

The complexes may be packaged in liquid form, in ampules as a solution in physiological glucose-saline solution, or albumin-containing saline solutions. They may also be packaged in dry form as a powder in admixture with human albumin, prepared by lyophilizing a solution of the complex with albumin.

Other embodiments and modifications will be apparent to those skilled in the art.

We claim:

1. A plasmin light (B) chain separated from the heavy (A) chain in its parent plasmin, said light (B) chain having proteolytic activity and having a serine protease active site.

2. The plasmin light (B) chain of claim 1 wherein said light (B) chain is derived from a parent plasmin having proteolytic activity and said light (B) chain has less proteolytic activity than the parent plasmin on an equal molar basis.

3. The plasmin light (B) chain of claim 2 wherein said parent plasmin is human plasmin.

4. The plasmin light (B) chain of claim 3 wherein said parent human plasmin is prepared from plasminogen which has been heat treated to inactivate viral contaminants.

5. A substantially equimolar complex of streptokinase and a plasmin light (B) chain having proteolytic activity and having a serine protease active site.

6. The complex of claim 5 wherein said plasmin light (B) chain constituent is derived from a parent plasmin having proteolytic activity and said complex has less proteolytic activity than the equimolar complex of streptokinase with said parent plasmin on an equal molar basis.

7. The complex of claim 6 wherein said plasmin light (B) chain constituent is derived from human plasmin.

8. The complex of claim 7 wherein said human plasmin is prepared from plasminogen which has been heat treated to inactivate viral contaminants.

9. The complex of claim 5 wherein said complex is a reaction product of streptokinase with a plasmin light (B) chain.

10. The complex of claim 5 wherein said complex is a fraction of a reduction product of an equimolar complex of streptokinase with plasminogen or plasmin.

11. The complex of claim 10 having a bovine plasminogen activator activity, measured on a casein substrate from about 100 to about 600 CTA units/nmol protein.

12. A method of preparing a plasmin light (B) chain with a serine protease active site which comprises mixing plasmin with a reversible serine protease active site inhibitor, reducing at the interchain disulfide bonds of the plasmin molecules in said mixture to produce a mixture containing heavy (A) and light (B) chains, and thereafter separating said light (B) chain from said heavy (A) chain.

13. The method of claim 12 wherein said mixture of heavy (A) and light (B) chains is alkylated prior to said separation.

14. The method of claim 13 wherein said alkylation is carried out with an alkylating agent of the group consisting of sodium iodoacetate and iodoacetamide.

15. The method of claim 12 wherein said plasmin is human plasmin.

16. The method of claim 15 wherein said human plasmin is prepared from plasminogen which has been heat treated to inactivate viral contaminants.

17. The method of claim 12 wherein said serine protease inhibitor is a member of the group consisting of leupeptin and benzamidine.

18. The method of claim 12 wherein said separation step is carried out by affinity chromatographic adsorption.

19. The method of claim 18 wherein said affinity chromatographic adsorption is carried out on a L-lysine-substituted adsorption material and wherein said light (B) chain is not adsorbed.

20. The method of claim 18 wherein said affinity chromatographic adsorption material is a member of the group consisting of L-lysine-substituted Sepharose, L-lysine-substituted polyacrylamide and L-lysine-substituted agarose, L-arginine-substituted Sepharose, L-arginine-substituted polyacrylamide, L-arginine-substituted agarose, D-lysine-substituted Sepharose, D-lysine-substituted polyacrylamide and D-lysine-substituted agarose.

21. A method of preparing a plasmin light (B) chain with a serine protease active site which comprises mixing human plasmin prepared from plasminogen which has been heat treated at at least 60° C. for at least ten hours with leupeptin, reducing said reaction product with 2-mercaptoethanol to produce a mixture of heavy (A) and light (B) chains, alkylating said mixture with sodium iodoacetate, and thereafter separating said light (B) chain from said heavy (A) chain by elution through a L-lysine-substituted Sepharose column and recovering of said light (B) chain in the unadsorbed fraction.

22. A method of preparing a complex of streptokinase and a plasmin light (B) chain having a serine protease active site which comprises reacting the light (B) chain product of the method of claim 12 with a substantially equimolar amount of streptokinase.

23. The method of claim 22 wherein about 1.0 mols of light (B) chain is reacted with about 0.9 mols of streptokinase.

24. The method of claim 22 wherein said mixture of heavy (A) and light (B) chains is alkylated prior to said separation step.

25. The method of claim 24 wherein said alkylation is carried out with an alkylating agent of the group consisting of sodium iodoacetate and iodoacetamide.

26. A method of preparing a complex of streptokinase and a plasmin light (B) chain having a serine protease active site which comprises mixing human plasmin prepared from plasminogen which has been heat treated at at least 60° C. for at least 10 hours, with leupeptin, reducing said reaction product with 2-mercaptoethanol to produce a mixture of heavy (A) and light (B) chains, alkylating said mixture with sodium iodoacetate, separating said light (B) chain from said heavy (A) chain by elution through a L-lysine-substituted Sepharose column and recovering said light (B) chain in the unadsorbed fraction and thereafter reacting said recovered light (B) chain with streptokinase in a mol ratio of about 1.0 mol of light (B) chain to about 0.9 mols of streptokinase.

27. A method of preparing a complex of streptokinase and a plasmin light (B) chain having a serine protease active site which comprises reacting a substance of the group consisting of human plasminogen which has been heat treated at at least 60° C. for at least 10 hours, and plasmin prepared from human plasminogen which has been heat treated at at least 60° C. for at least ten hours, with an approximately equimolar amount of streptokinase to produce a streptokinase complex therewith, reducing said reaction product at the interchain disulfide bonds of the plasmin molecules to produce a heavy (A) chain and a light (B) chain-streptokinase complex and thereafter separating said light (B) chain-streptokinase complex from said heavy (A) chain.

28. The method of claim 27 wherein said mixture of heavy (A) chain and light (B) chain-streptokinase complex is alkylated prior to said separation step.

29. The method of claim 28 wherein said alkylation is carried out with an alkylating agent of the group consisting of sodium iodoacetate and iodoacetamide.

30. The method of claim 27 wherein said separation step is carried out by affinity chromatographic adsorption.

31. The method of claim 27 wherein said affinity chromatographic adsorption is carried out on a L-lsyine-substituted adsorption material and wherein said light (B) chain-streptokinase complex is not adsorbed.

32. The method of claim 31 wherein said affinity chromatographic adsorption material is a member of the group consisting of L-lysine-substituted Sepharose, L-lysine-substituted polyacrylamide and L-lysine-substituted agarose, L-arginine-substituted Sepharose, L-arginine-substituted polyacrylamide, L-arginine-substituted agarose, D-lysine-substituted Sepharose, D-lysine-substituted polyacrylamide and D-lysine-substituted agarose.

* * * * *